United States Patent [19]

Clark

[11] Patent Number: 5,695,774
[45] Date of Patent: Dec. 9, 1997

[54] USE OF NABUMETONE OR 6-METHOXYNAPHTHYL ACETIC ACID FOR THE TREATMENT OF DEMENTIA

[75] Inventor: Michael Sidney George Clark, Much Hadham, United Kingdom

[73] Assignee: SmithKline Beecham p.l.c., Brentford, England

[21] Appl. No.: 578,586

[22] PCT Filed: Jul. 11, 1994

[86] PCT No.: PCT/EP94/02300

§ 371 Date: Jan. 3, 1996

§ 102(e) Date: Jan. 3, 1996

[87] PCT Pub. No.: WO95/02399

PCT Pub. Date: Jan. 26, 1995

[30] Foreign Application Priority Data

Jul. 15, 1993 [GB] United Kingdom ............... 9314693

[51] Int. Cl.⁶ ..................................................... A61K 9/20
[52] U.S. Cl. ........................ 424/464; 424/465; 424/468; 424/489; 514/682

[58] Field of Search ..................... 424/464, 331, 424/489, 468, 465; 514/682

[56] References Cited

U.S. PATENT DOCUMENTS

| | | | |
|---|---|---|---|
| 4,061,779 | 12/1977 | Lake et al. | 514/682 |
| 4,420,639 | 12/1983 | Lake et al. | 568/328 |
| 5,192,753 | 3/1993 | McGeer et al. | 514/159 |

FOREIGN PATENT DOCUMENTS

| | | |
|---|---|---|
| 8487M | 7/1973 | France . |
| WO92/04019 | 3/1992 | WIPO . |

OTHER PUBLICATIONS

The Lancet, vol. 335, No. 8696, 28 Apr. 1990.

*Primary Examiner*—Thurman K. Page
*Assistant Examiner*—William E. Benston, Jr.
*Attorney, Agent, or Firm*—Stephen Venetianer; Edward T. Lentz

[57] ABSTRACT

The present invention relates to a method for the treatment of cognitive disorders such as alzheimer disease and to a compound for use in such method.

7 Claims, No Drawings

USE OF NABUMETONE OR 6-METHOXYNAPHTHYL ACETIC ACID FOR THE TREATMENT OF DEMENTIA

This application is a 371 of PCT/EP94/02300, filed Jul. 11, 1994.

The present invention relates to a method for the treatment of cognitive disorders such as alzheimers disease and to a compound for use in such method.

U.S. Pat. No. 4,420,639 describes 4-(6'-methoxy-2'-naphthyl)butan-2-one (nabumetone) and its use in the treatment of rheumatic and arthritic conditions. It is known that the active metabolite of nabumetone is 6-methoxynaphthyl acetic acid or 6MNA. It should be appreciated that the term 6MNA also includes pharmaceutically acceptable salts thereof.

U.S. Pat. No. 5,192,753 (McGeer) describes the use of NSAID's to treat dementia, however, there is no mention of nabumetone in this patent.

It has now been discovered that nabumetone has potential therapeutic utility for treating and/or prevention of dementia such as alzheimers disease.

Accordingly, the present invention provides a method for treating and/or preventing dementia such as alzheimers disease in human or non-human animals, which comprises administering an effective, non-toxic amount of nabumetone or 6MNA, to human or non-human animals in need thereof.

The present invention also provides the use of nabumetone or 6MNA in the manufacture of a medicament for use in the treatment and/or prevention of dementia such as alzheimers disease.

A nabumetone or 6MNA medicament, for use in the treatment and/or prevention of dementia such as alzheimers disease may be prepared by admixture of nabumetone or 6MNA with an appropriate carrier, which may contain a diluent, binder, filler, disintegrant, flavouring agent, colouring agent, lubricant or preservative in conventional manner.

Preferably, the medicament is in unit dosage form and in a form adapted for use in the medical or veterinarial fields. For example, such preparations may be in a pack form accompanied by written or printed instructions for use as an agent in the treatment and/or prevention of dementia such as alzheimers disease.

The suitable dosage range for nabumetone or 6MNA depends on the severity of the dementia such as alzheimers disease and on the condition of the patient. It will also depend, inter alia, upon the relation of potency to absorbability and the frequency and route of administration.

Nabumetone or 6MNA may be formulated for administration by any route, and examples are oral, rectal, topical, parenteral, intravenous or intramuscular administration. Preparations may, if desired, be designed to give slow release of nabumetone.

The medicaments may, for example, be in the form of tablets, dispersible tablets, capsules, sachets, vials, powders, granules, lozenges, reconstitutable powders, or liquid preparations, for example solutions or suspensions, or suppositories.

The medicaments, for example those suitable for oral administration, may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycerine; tabletting lubricants, for example magnesium stearate; disintegrants, for example starch, polyvinylpyrrolidone, sodium starch glycollate or microcrystalline cellulose; or pharmaceutically acceptable setting agents such as sodium lauryl sulphate.

Solid medicaments may be obtained by conventional methods of blending, filling, tabletting or the like. Repeated blending operations may be used to distribute nabumetone throughout those medicaments employing large quantities of fillers. When the medicament is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in normal pharmaceutical practice, in particular with an enteric coating. The medicament may also be in the form of an ingestible capsule, for example of gelatin containing nabumetone if desired with a carrier or other excipients.

Medicaments for oral administration as liquids may be in the form of, for example, emulsions, syrups, or elixirs, or may be presented as a dry product for reconstitution with water or other suitable vehicle before use. Such liquid medicaments may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; aqueous or non-aqueous vehicles, which include edible oils, for example almond oil, fractionated coconut oil, oily esters, for example esters of glycerine, or propylene glycol, or ethyl alcohol, glycerine, water or normal saline; preservatives, for example methyl or propyl p-hydroxybenzoate or sorbic acid; and if desired conventional flavouring or colouring agents.

Nabumetone or 6MNA may also be administered by a non-oral route. In accordance with routine pharmaceutical procedure, the medicaments may be formulated, for example for rectal administration as a suppository. They may also be formulated for presentation in an injectable form in an aqueous or non-aqueous solution, suspension or emulsion in a pharmaceutically acceptable liquid, e.g. sterile pyrogen-free water or a parenterally acceptable oil or a mixture of liquids. The liquid may contain bacteriostatic agents, anti-oxidants or other preservatives, buffers or solutes to render the solution isotonic with the blood, thickening agents, suspending agents or other pharmaceutically acceptable additives. Such forms will be presented in unit dose form such as ampoules or disposable injection devices or in multi-dose forms such as a bottle from which the appropriate dose may be withdrawn or a solid form or concentrate which can be used to prepare an injectable formulation.

As mentioned hereinbefore, the effective dose of nabumetone or 6MNA depends on the severity of the alzheimers disease the condition of the patient and on the frequency and route of administration. A unit dose will generally contain from 20 to 2000 mg and preferably will contain from 30 to 1000 mg, in particular 50, 100, 150, 200, 250, 300, 350, 400, 450, 500, 750, 800 or 1000 mg. The composition may be administered once or more times a day for example 2, 3 or 4 times daily, and the total daily dose for a 70 kg adult will normally be in the range 100 to 3000 mg. Alternatively the unit dose will contain from 2 to 20 mg of nabumetone and be administered in multiples, if desired, to give the preceding daily dose.

Most preferably nabumetone compositions are in the form of 500 mg or 1000 mg swallow tablets.

The present invention further provides a pharmaceutical composition for use in the treatment and/or prevention of dementia such as alzheimers disease which comprises an effective amount of nabumetone or 6MNA and a pharmaceutically acceptable carrier. Such compositions may be prepared in the manner as hereinbefore described.

The invention may be illustrated by carrying out clinical investigations conventional in the field of assessing dementia drugs such as these mentioned in U.S. Pat. No. 5,192,753.

I claim:

1. A method for the treatment of dementia in human or non-human animals, which comprises administering a non-toxic amount of nabumetone or 6MNA to a sufferer in need thereof.

2. A method according to claim 1 wherein the dementia is alzheimer's disease.

3. A method according to claim 1 the nabumetone or 6MNA is orally administered.

4. A method according to claim 1 wherein the nabumetone or 6MNA is parentally administered.

5. A method according to claim 1 wherein the nabumetone or 6MNA is topically administered.

6. A method according to claim 1 wherein the nabumetone or 6MNA is in the unit dose composition containing from 20 to 2000 mg of nabumetone or 6MNA.

7. A method according to claim 1 wherein the nabumetone or 6MNA is in the form of a swallow tablet composition containing 500 mg to 1000 mg of nabumetone or 6MNA.

* * * * *